(12) United States Patent
Wolfgramm

(10) Patent No.: US 12,109,351 B2
(45) Date of Patent: *Oct. 8, 2024

(54) VAVD REGULATOR CONTAMINATION AND CONDENSATION CONTROL

(71) Applicant: LivaNova Deutschland GmbH, Munich (DE)

(72) Inventor: Olivier Wolfgramm, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/242,733

(22) Filed: Sep. 6, 2023

(65) Prior Publication Data
US 2023/0414857 A1   Dec. 28, 2023

Related U.S. Application Data

(63) Continuation of application No. 18/101,276, filed on Jan. 25, 2023, now Pat. No. 11,819,603, which is a
(Continued)

(51) Int. Cl.
*A61M 1/00* (2006.01)
*A61M 1/36* (2006.01)

(52) U.S. Cl.
CPC ............ *A61M 1/743* (2021.05); *A61M 1/785* (2021.05); *A61M 1/3666* (2013.01);
(Continued)

(58) Field of Classification Search
CPC .... A61M 1/743; A61M 1/785; A61M 1/3666; A61M 2205/3331; A61M 2205/3368;
(Continued)

(56) References Cited

U.S. PATENT DOCUMENTS 3,474,907 A   10/1969 Cary et al.
4,490,331 A   12/1984 Steg, Jr.
(Continued)

FOREIGN PATENT DOCUMENTS

JP   2016153308 A   8/2016
WO   0044415 A1   8/2000
(Continued)

OTHER PUBLICATIONS

International Search Report and Written Opinion received for PCT Patent Application No. PCT/EP2017/075451, dated Jun. 11, 2018, 11 pages.
(Continued)

*Primary Examiner* — Nicholas J. Weiss
*Assistant Examiner* — Brandon W. Levy
(74) *Attorney, Agent, or Firm* — Seager, Tufte & Wickhem LLP

(57) ABSTRACT

Embodiments include a vacuum assisted venous drainage (VAVD) system, including a regulator valve assembly configured to facilitate application of vacuum to a reservoir; a control unit configured to control the regulator valve assembly to facilitate controlling application of the vacuum; at least one pressure sensor coupled to the reservoir and configured to obtain pressure measurements of pressure in the reservoir; a heating element configured to heat the regulator valve assembly to a target temperature; and at least one temperature sensor configured to determine a temperature of the regulator valve assembly.

19 Claims, 3 Drawing Sheets

Related U.S. Application Data continuation of application No. 16/753,751, filed as application No. PCT/EP2017/075451 on Oct. 6, 2017, now Pat. No. 11,590,274.

(52) U.S. Cl.
CPC ............... *A61M 2205/3331* (2013.01); *A61M 2205/3368* (2013.01); *A61M 2205/3584* (2013.01); *A61M 2205/36* (2013.01); *A61M 2205/3673* (2013.01); *A61M 2205/52* (2013.01); *A61M 2205/7536* (2013.01)

(58) Field of Classification Search
CPC ...... A61M 2205/3584; A61M 2205/36; A61M 2205/3673; A61M 2205/52; A61M 2205/7536; A61M 1/73; A61M 1/3627; A61M 1/1686; A61M 1/14; A61M 1/3621; A61M 1/3609; A61M 1/166; A61M 1/1629; A61M 2202/0413; A61M 2205/128; A61M 60/892; A61M 60/894; A61L 2/04; A61L 2202/122; A61L 2/00–28; Y10T 137/6606; F16K 49/002
See application file for complete search history.

(56) References Cited

U.S. PATENT DOCUMENTS

| | | |
|---|---|---|
| 4,599,093 A | 7/1986 | Steg, Jr. |
| 5,094,260 A | 3/1992 | Stuart et al. |
| 5,823,986 A | 10/1998 | Peterson |
| 7,335,334 B2 | 2/2008 | Olsen et al. |
| 7,922,683 B2 | 4/2011 | Ogihara et al. |
| 8,147,440 B2 | 4/2012 | Tamari |
| 9,044,555 B2 | 6/2015 | Hannan et al. |
| 2002/0147100 A1 | 10/2002 | Malcolm et al. |

FOREIGN PATENT DOCUMENTS

| | | |
|---|---|---|
| WO | 03030790 A1 | 4/2003 |
| WO | 2012161744 A2 | 11/2012 |
| WO | 2013190381 A1 | 12/2013 |

OTHER PUBLICATIONS

Toba, Drinking water supply device, 2013. Google Patents (Year:2013).

VAVD REGULATOR CONTAMINATION AND CONDENSATION CONTROL

CROSS REFERENCE TO RELATED APPLICATION

This application is a continuation of U.S. patent application Ser. No. 18/101,276, filed Jan. 25, 2023, which is a continuation of U.S. patent application Ser. No. 16/753,751, filed Apr. 3, 2020, which is a National Stage Application of PCT/EP2017/075451, filed Oct. 6, 2017, which are herein incorporated by reference in their entirety.

TECHNICAL FIELD

The present disclosure relates to vacuum-assisted drainage devices and methods. More specifically, the disclosure relates to vacuum assisted venous drainage (VAVD) systems and methods.

BACKGROUND

Vacuum control in blood reservoirs may be utilized in a number of different drainage systems, perfusion systems, heart-lung machines, and/or the like. These systems may include vacuum assisted venous drainage (VAVD) systems. A problem often encountered during operation of VAVDs is the deterioration of vacuum regulators due to water vapor present in the air aspirated from the reservoir, which may create condensation inside the valve assembly. Additionally, after use, humidity left in the regulators offers an opportunity for molds and bacteria to grow. Conventional regulators often must be disinfected with potentially aggressive substances on a regular basis, causing potential further deterioration of the regulators.

SUMMARY

Example 1 is a vacuum assisted venous drainage (VAVD) system, including a regulator valve assembly configured to facilitate application of vacuum to a reservoir; a control unit configured to control the regulator valve assembly to facilitate controlling application of the vacuum; at least one pressure sensor coupled to the reservoir and configured to obtain pressure measurements of pressure in the reservoir; a heating element configured to heat the regulator valve assembly to a target temperature; and at least one temperature sensor configured to determine a temperature of the regulator valve assembly.

Example 2 is the system of Example 1 wherein the control unit is configured to perform, using the heating element, a thermal disinfection cycle to disinfect the regulator valve assembly.

Example 3 is the system of Example 1 or 2 wherein the control unit is configured to perform, using the regulator valve assembly, an operational task, and maintain, using the heating element and during performance of at least a portion of the operational task, the temperature of the regulator valve assembly at a target temperature.

Example 4 is the system of any of Examples 1-3 wherein the control unit is configured to maintain the temperature by heating the valve assembly to a target temperature and maintaining the valve assembly at the target temperature for a specified duration.

Example 5 is the system of any of Examples 1-4 further including a cooling element configured to cool the regulator valve assembly to a cooling temperature.

Example 6 is the system of Example 5 wherein the cooling element is the heating element.

Example 7 is the system of any of Examples 1-6 wherein the heating element is a Peltier element.

Example 8 is the system of any of Examples 5-7 wherein the control unit is further configured to facilitate cooling the regulator valve assembly, using the cooling element, to a cooling temperature, the cooling temperature being a temperature selected to prevent condensation on inner surfaces of the valve assembly in response to contact with aspirated air.

Example 9 is the system of any of Examples 1-8 wherein the control unit is configured to facilitate maintaining the temperature by utilizing at least one of a look-up table and a feedback control mechanism.

Example 10 is the system of Example 9 wherein the feedback control mechanism is a proportional integral derivative (PID) algorithm.

Example 11 is a method, performed by a regulator for controlling vacuum in a reservoir to facilitate vacuum assisted venous drainage (VAVD), the method including performing a thermal disinfection cycle, performing an operational task, and maintaining, during performance of at least a portion of the operational task, the temperature of the regulator valve assembly at a target temperature.

Example 12 is the method of Example 11 wherein maintaining the temperature utilizes electrical heating or a Peltier element.

Example 13 is the method of Examples 11 or 12 wherein maintaining the temperature includes heating the valve assembly to a target temperature and maintaining the valve assembly at the target temperature for a specified duration.

Example 14 is the method of any of Examples 11-13 further including facilitating cooling the valve assembly to a cooling temperature, the cooling temperature being a temperature selected to prevent condensation on inner surfaces of the valve assembly in response to contact with aspirated air.

Example 15 is the method of any of Examples 11-14 wherein facilitating cooling the valve assembly is performed by controlling a Peltier element.

Example 16 is the method of any of Examples 11-15 wherein maintaining the temperature utilizes at least one of a look-up table and a feedback control mechanism.

Example 17 is the method of Example 16 wherein the feedback control mechanism is a proportional integral derivative (PID) algorithm.

Example 18 is the method of any of Examples 11-17 further comprising directly measuring the pressure in the reservoir.

Example 19 is the method of Example 18 wherein directly measuring the pressure utilizes a sensing tube directly connected to the reservoir.

Example 20 is a vacuum assisted venous drainage (VAVD) system, including a regulator valve assembly configured to facilitate application of vacuum to a reservoir, a control unit configured to control the regulator valve assembly to facilitate controlling application of the vacuum, at least one pressure sensor coupled to the reservoir and configured to obtain pressure measurements of pressure in the reservoir, a heating element configured to heat the regulator valve assembly to a target temperature, the heating element comprising a cooling element, and at least one temperature sensor configured to determine a temperature of the regulator valve assembly.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
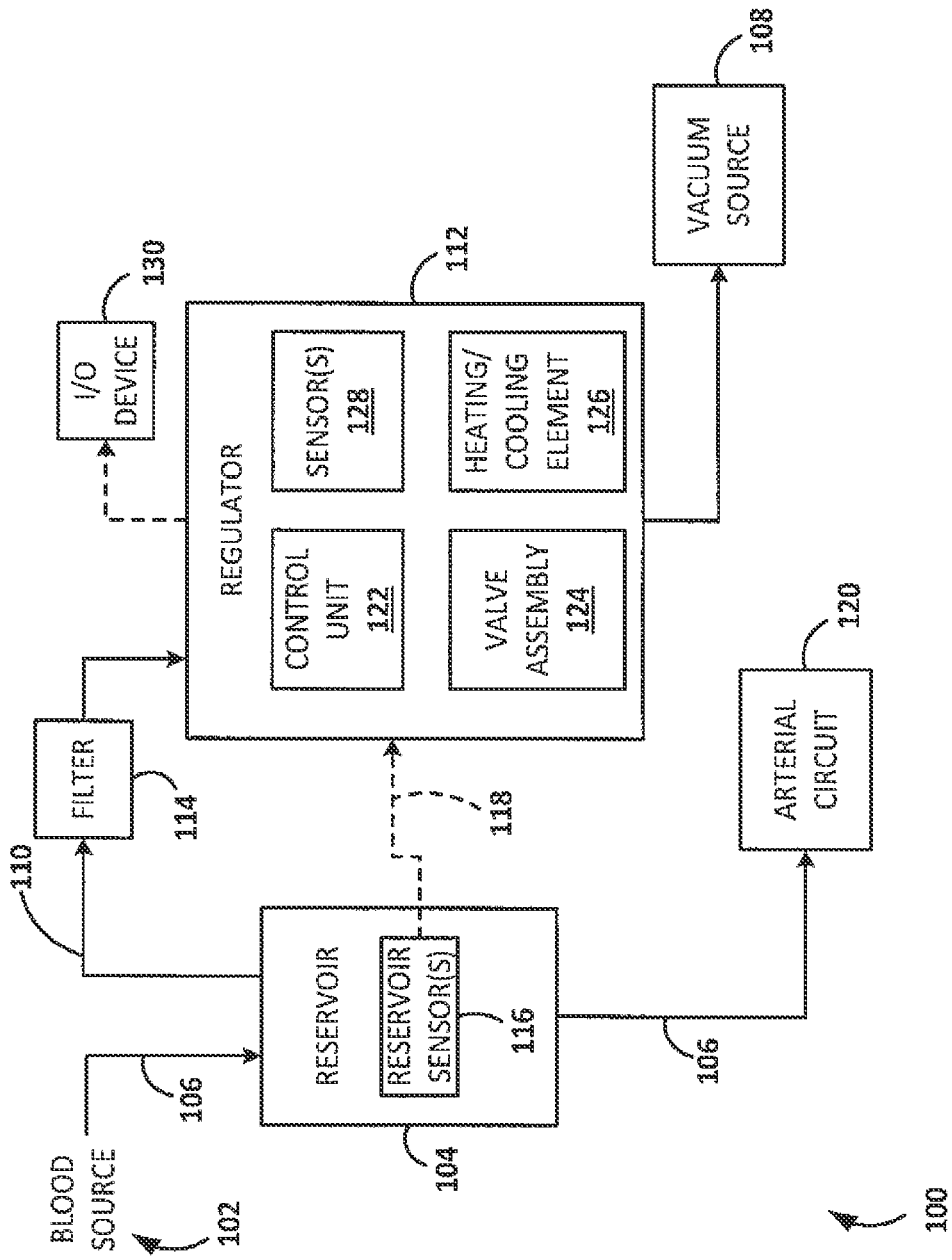
FIG. 1 is a schematic block diagram of an illustrative vacuum assisted venous drainage system, in accordance with embodiments of the disclosed subject matter.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

Embodiments include a vacuum assisted venous drainage (VAVD) system that includes a regulator having a valve assembly and a control unit. The regulator also includes a heating and/or cooling element ("heating/cooling element") configured to heat and/or cool the valve assembly. The control unit controls the valve assembly and the heating/cooling element. Any number of different sensors may be configured to provide information to the control unit. In embodiments, the regulator may be configured to heat the valve assembly automatically at start-up. In embodiments, the regulator is configured to heat and/or cool its valve assembly by means of electrical heating and/or indirectly by Peltier element. The regulator may also be configured to perform an auto-diagnosis on its systems. While facilitating operational tasks, the regulator may be configured to maintain the valve assembly at a target temperature.

According to embodiments, the regulator may be precisely controlled with a combination of look up tables and control algorithms (e.g., control loop feedback mechanisms such as, for example, PID algorithms), able to set and maintain the pressure in the reservoir at a level requested by an operator or other system component. The pressure may be directly measured in the reservoir in a redundant way, such as, for example, by a sensing tube directly connected to the reservoir. The redundant measuring system may be configured to facilitate enabling the regulator to automatically detect malfunctioning due to clogs, kinked tubes, and/or the like.

FIG. 1 is a schematic block diagram that depicts an illustrative vacuum assisted venous drainage (VAVD) system 100, in accordance with embodiments of the disclosed subject matter. As shown in FIG. 1, the VAVD system 100 may be configured to facilitate moving blood from a blood source 102 (e.g., a patient, a part of a heart-lung machine, a part of a perfusion system, etc.) into a reservoir 104 via an intake line 106 by applying a vacuum to the reservoir 104 using a vacuum source 108 connected to the reservoir 104 via a vacuum line 110. In FIG. 1, the vacuum line 110 is attached to the vacuum port of the venous reservoir 104, connecting the venous reservoir 104 to the vacuum source 108. The system includes a vacuum regulator 112 configured to facilitate application of a vacuum to the reservoir 104. The illustrated system 100 includes a filter 114, disposed downstream of the reservoir 104 and upstream of the vacuum regulator 112, that is configured to prevent fluid from passing into the vacuum regulator 112 and/or vacuum source 108. In embodiments, for example, the filter 114 may be a hydrophobic filter 114. In other embodiments, the system 100 may not include a filter 114.

The system 100 may include one or more sensors 116 associated with (e.g., disposed within, coupled to, etc.) the reservoir 104 and communicatively coupled, via a communication link 118. The sensor(s) 116 may include one or more level sensors, one or more vacuum sensors, one or more temperature sensors, and/or the like. In embodiments, for example, the vacuum regulator 112 may be configured to provide continuously adjustable control of the vacuum level in the venous reservoir 104 as measured, for example, by one or more vacuum sensors 116 configured to directly measure a vacuum level of the reservoir 104—that is, the vacuum sensor or sensors 116 obtain measurements through a physical interface on and/or within the reservoir 104. In embodiments, a vacuum sensor may be a sensing tube connected directly to the reservoir so that a physical interface of the sensor 116 is exposed to an environment within the reservoir 104. The system 100 may include other pressure sensors (e.g., along various portions of the vacuum line and/or blood line) to provide redundant pressure measurements.

In embodiments, the communication link 118 may be, or include, a wired link, a wireless communication link such as, for example, a short-range radio link, such as Bluetooth, IEEE 802.11, a proprietary protocol, and/or the like. The term "communication link" may refer to an ability to communicate some type of information in at least one direction between at least two locations, and should not be understood to be limited to a direct, persistent, or otherwise limited communication channel. That is, according to embodiments, the communication link 118 may be a persistent communication link, an intermittent communication link, an ad-hoc communication link, and/or the like. The communication link 118 may refer to direct communications between the sensor(s) 116 and the regulator 112, and/or indirect communications that travel between the sensor(s) 116 and the regulator 112 via at least one other device (e.g., a repeater, router, hub, and/or the like). The communication link 118 may facilitate uni-directional and/or bi-directional communication between the sensor(s) 116 and the regulator 112.

In embodiments, the vacuum regulator 112 may be configured to provide level control within the venous reservoir 104. For example, the reservoir 104 may be provided with one or more level sensors configured to sense a level of blood and/or other fluid within the reservoir 104. The sensed level can be used to activate alarms at the user interface indicative of, for example, full reservoir, empty reservoir, low level, and/or the like. The sensed level can also be used in the closed loop feedback control of other parts of a perfusion system which affect (and/or are affected by) the level of blood in the reservoir 104. For example, in embodiments portions of an arterial circuit 120, disposed downstream of the reservoir 104, may be controlled based on sensed parameters such as, for example, pressure, level, temperature, and/or the like.

As shown in FIG. 1, the regulator 112 includes a control unit 122 configured to control operation of a regulator valve assembly 124 and a heating/cooling element 126 that is configured to heat and/or cool the valve assembly 124. In embodiments, for example, the heating/cooling element 126 may include a Peltier element configured to heat and/or cool the valve assembly 124. The regulator 112 may include any number of different types of sensors 128 configured to sense parameters such as, for example, temperature, pressure, and/or the like. In this manner, the control unit 122 may be configured to control the valve assembly 124 to facilitate controlling application of the vacuum applied to the reservoir 104.

Additionally, the control unit may be configured to control a heating element 126 configured to heat the regulator valve assembly 124 to a target temperature; and at least one temperature sensor 128 configured to determine a temperature of the regulator valve assembly to facilitate maintenance of a target temperature. In embodiments, a target temperature may include a specified temperature, a range of temperatures, a threshold temperature, and/or the like. In embodiments, the control unit 122 may be configured, for example, to perform (e.g., at start-up), using a heating element 126, a thermal disinfection cycle to disinfect the regulator valve assembly 124. In embodiments, following the disinfection cycle, the control unit may be configured to perform, using the regulator valve assembly, an operational task; and maintain, using the heating element and during performance of at least a portion of the operational task, the temperature of the regulator valve assembly at a target temperature. In embodiments, the heating element 126 may be inserted into the valve assembly 124, attached to the valve assembly 124 externally, be integrated with the valve assembly 124, and/or the like. In embodiments, power loss from one or more valves may be captured and used for heating the valve assembly 124.

For example, in embodiments, the control unit 122 may be configured to maintain the temperature by heating the valve assembly 124 to a target temperature and maintaining the valve assembly 124 at the target temperature (or at another target temperature) for some specified period of time. For example, in embodiments, the control unit 122 may be configured to maintain the temperature by heating the valve assembly 124 to a target temperature of at least approximately 90 degrees Celsius; and maintaining the valve assembly 124 at the target temperature for between approximately two minutes and approximately 5 minutes. In embodiments, the control unit may be configured to facilitate maintaining the temperature by maintaining the valve assembly 124 at an operating temperature of approximately 70 degrees Celsius. According to various embodiments, the target temperature may include any temperature, temperature range, and/or the like; and the specified time period for maintaining a target temperature may, likewise, include any time period. For example, in embodiments, the valve assembly 124 may be constructed of materials that can withstand higher temperatures, in which case the control unit 122 may be configured to take advantage of that capability by heating the valve assembly 124 to higher temperatures that can be handled.

In embodiments, the control unit 122 may be configured to use a cooling element to cool the regulator valve assembly to a cooling temperature. The cooling element may be, include, or be included in the heating element, and may include, in embodiments, a Peltier element. In this manner, for example, the control unit 122 may be further configured to facilitate cooling the regulator valve assembly 124, using the cooling element 126, to a cooling temperature, the cooling temperature being a temperature selected to prevent condensation on inner surfaces of the valve assembly 124 in response to contact with aspirated air. According to various embodiments, the control unit 122 may be configured to facilitate changing and/or maintaining the temperature by utilizing at least one of a look-up table and a control mechanism such as, for example, a PID algorithm, a PI algorithm, a fuzzy control algorithm, and/or the like.

According to embodiments, the control unit 122 may include a processing unit configured to communicate with memory to execute computer-executable instructions stored in the memory. In embodiments, the control unit 122 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the control unit 122 is referred to herein in the singular, the control unit 122 may be implemented in multiple instances, distributed across multiple computing devices, instantiated within multiple virtual machines, and/or the like.

The system 100 may also include an I/O device 130, which may refer to one or more I/O devices 130 and may include any number of different types of I/O devices such as, for example, light indicators, speakers, buttons, and/or the like. The I/O device 130 may be configured to present information to a user and/or receive input from a user. According to embodiments, the I/O device 130 may be configured to indicate a device status (e.g., on/off, active, error, etc.), receive a command from a user, and/or the like. In embodiments, the I/O device 130 may include a touchscreen interface, an LED, and/or the like.

According to various embodiments of the disclosed subject matter, any number of the components depicted in FIG. 1 (e.g., the control unit 122, the I/O device 130, aspects of the communication link 118, and/or the arterial circuit 120) may be implemented on one or more computing devices. A computing device may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "portable sampling devices," and the like, all of which are contemplated within the scope of FIG. 1, with reference to various components of the system 100.

In embodiments, a computing device includes a bus that, directly and/or indirectly, couples the following devices: a processing unit, a memory, an input/output (I/O) port, an I/O component, and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus represents what may be one or more busses (such as, for example, an address bus, data bus, or combination thereof). Similarly, in embodiments, the computing device may include a number of processing units, a number of memory components, a number of I/O ports, a number of I/O components, and/or a number of power supplies. Additionally any number of these components, or combinations thereof, may be distributed and/or duplicated across a number of computing devices.

In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware The illustrative VAVD system 100 shown in FIG. 1 is not intended to suggest any limitation as to the scope of use or functionality of embodiments of the present disclosure. The illustrative system 100 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
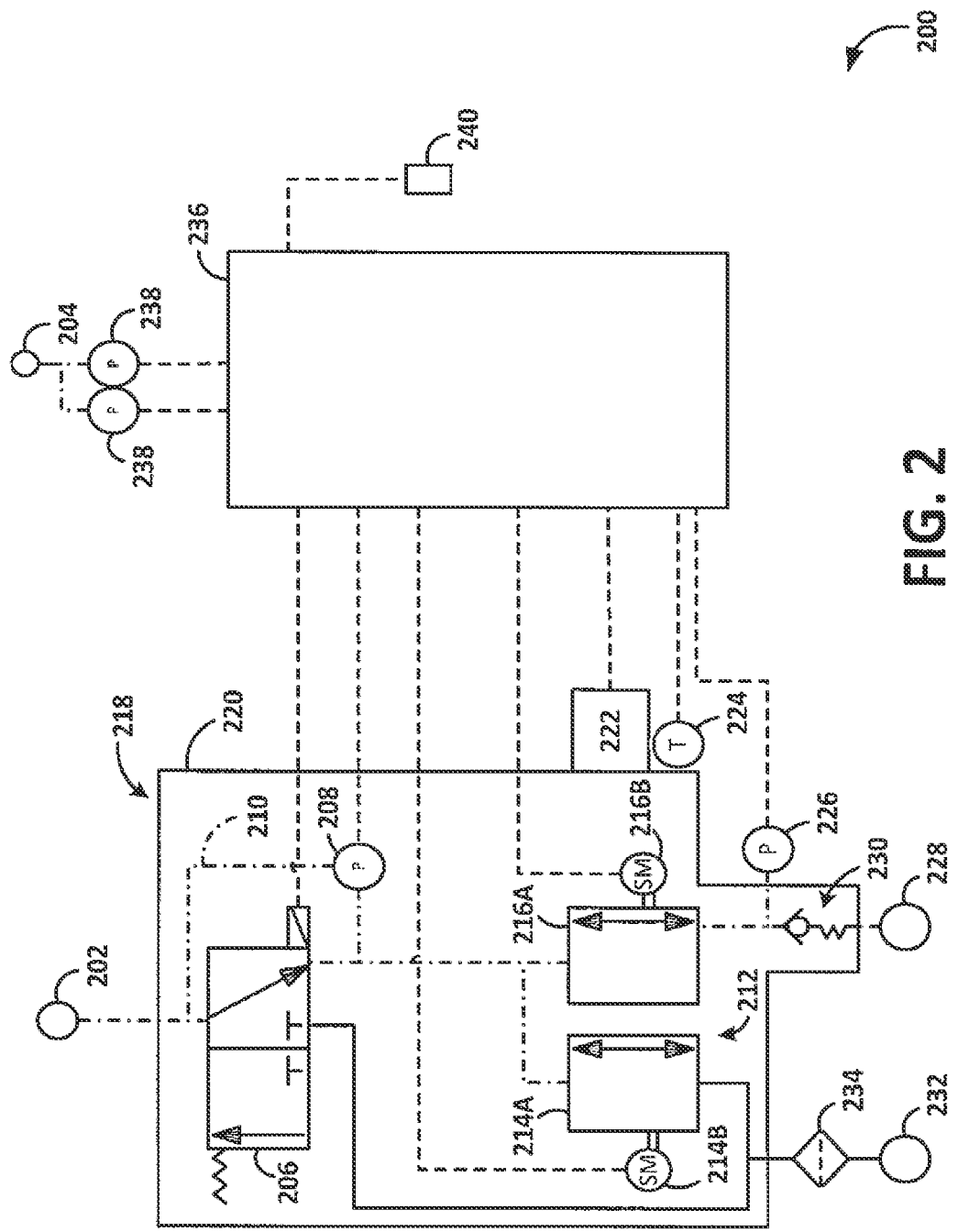
FIG. 2 is a schematic block diagram of an illustrative vacuum assisted venous drainage regulator, in accordance with embodiments of the disclosed subject matter.

FIG. 2 is a schematic block diagram depicting an illustrative vacuum regulator 200, in accordance with embodiments of the disclosed subject matter. In the diagram, solid connectors represent the blood/vacuum line and dashed connectors represent communication/power links. According to embodiments, the regulator 200 may be, be similar to, include, or be included in the regulator 112 depicted in FIG. 1. As shown in FIG. 2, the regulator 200 includes a vacuum port 202 configured to facilitate application of vacuum to a blood reservoir (e.g, the reservoir 104 depicted in FIG. 1); a sensor port 204 for connecting a pressure sensor that measures pressure (e.g., vacuum level) within the reservoir to the regulator 200; an emergency valve 206 configured to facilitate aerating the reservoir to ambient in the event that no power is present and/or a malfunction is detected; a pressure sensor 208 configured to be able to facilitate performing a self-diagnostic process of the regulator 200; and an alternative connection 210 to the pressure sensor 208.

As is further shown in FIG. 2, embodiments of the illustrative regulator 200 include a regulator valve assembly 212 (e.g., the regulator valve assembly 124 depicted in FIG. 1). In embodiments, the valve assembly 212 may include any number of different types of valves such as, for example, an atmospheric regulator valve 214A and/or a vacuum regulator valve 216A. As shown in FIG. 2, in embodiments, the valves 214A and 216A may include solenoid motor valve 214B and 216B, respectively. In other embodiments, the valves 214A and 216A may include any other mechanisms of operation. In embodiments, the valve assembly 212 may be integrated with, disposed within, or otherwise associated with a heated valve block 220 that is heated using a heating/cooling element 222 (e.g., the heating/cooling element 126 depicted in FIG. 1). A temperature sensor 224 may facilitate providing a feedback control loop for controlling and maintaining the temperature of the valve assembly 212.

As is also shown in FIG. 2, the regulator 200 may include a pressure sensor 226 configured to sense a level of vacuum provided by a vacuum source 228 (e.g., the vacuum source 108 depicted in FIG. 1); and a unidirectional valve 230 configured to protect against erroneous connection to a pressurized gas source. In embodiments, the regulator 200 may include a relief 232 to ambient air, along with a filter 234. The regulator 200 also may include a control unit 236 configured to control the valve assembly 212, the heating/cooling element 222, perform automated diagnostic process, and/or the like. The control unit 236 may be, be similar to, include, or be included within the control unit 122 depicted in FIG. 1. Additionally, as shown in FIG. 2, the regulator 200 may include one or more redundant pressure sensors 238 configured to sense vacuum level within the reservoir, and a power supply/control connector 240 to heart-lung machines, perfusion systems, and/or the like.

The illustrative regulator 200 shown in FIG. 2 is not intended to suggest any limitation as to the scope of use or functionality of embodiments of the present disclosure. The illustrative regulator 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
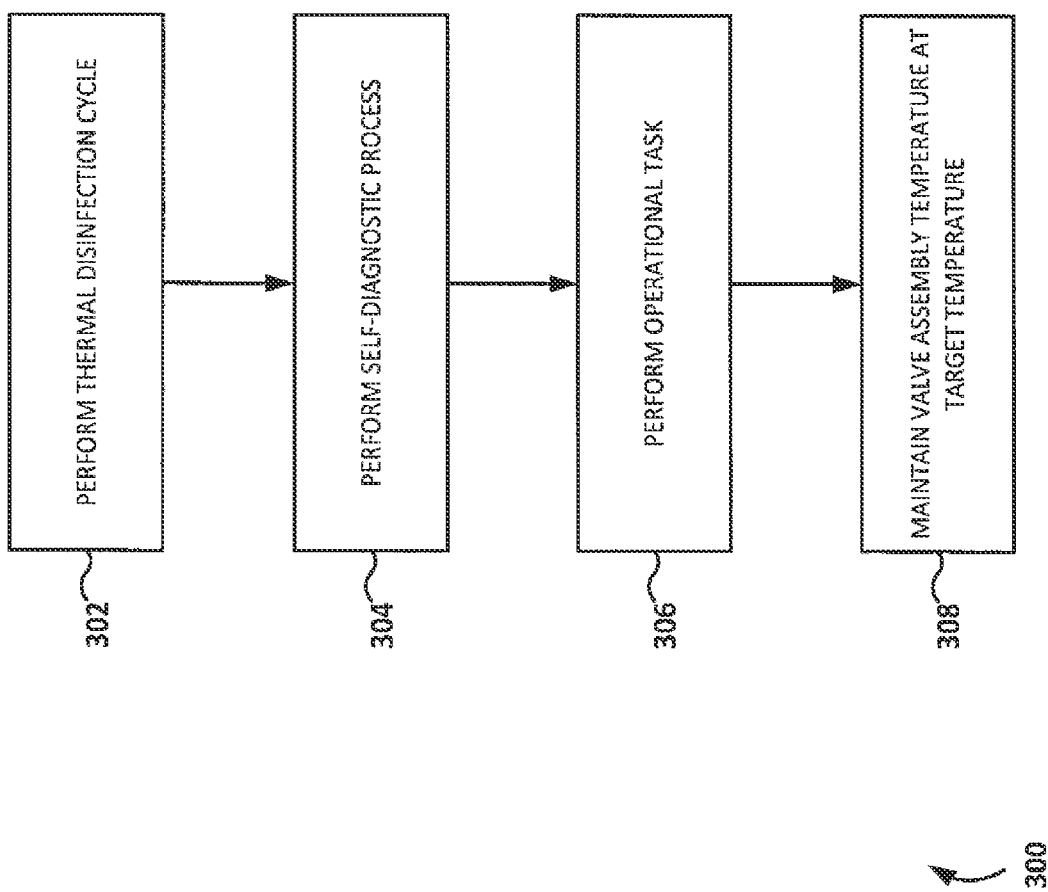
FIG. 3 is a flow diagram depicting an illustrative method of performing vacuum assisted venous drainage, in accordance with embodiments of the disclosed subject matter.

FIG. 3 is a flow diagram depicting an illustrative method 300, performed by a regulator for controlling vacuum in a reservoir to facilitate vacuum assisted venous drainage (VAVD). According to embodiments, aspects of the method may be performed by a regulator such as, for example, the regulator 112 depicted in FIG. 1 and/or the regulator 200 depicted in FIG. 2. As shown in FIG. 3, embodiments of the method 300 include performing a thermal disinfection cycle (block 302). For example, in embodiments, a regulator may perform a thermal disinfection cycle by causing a heating element to heat the regulator valve assembly to a target temperature (e.g., which may include any number of different target temperatures such as, for example, a temperature above approximately 90 degrees Celsius) and by facilitating maintaining the temperature of the regulator valve assembly at a target temperature for a target duration (e.g., which may be any number of different time periods such as, for example, between approximately three minutes and six minutes). In embodiments, the thermal cycle may include heating the valve assembly to a target temperature and holding that target temperature (or another target temperature) for a specified period of time. For example, in embodiments, the thermal heating cycle may include heating the valve assembly to a target temperature of above approximately 90 degrees Celsius and holding it at that temperature for up to 5 minutes (or more than 5 minutes, in embodiments), so as to disinfect the valve assembly by, for example, killing bacteria, mold, and/or the like. In embodiments, after the target duration elapses, the regulator may be configured to cool the regulator valve assembly to a cooling temperature, the cooling temperature being a temperature selected to prevent condensation on inner surfaces of the valve assembly in response to contact with aspirated air.

According to embodiments, the regulator may include an emergency shut-off system configured to prevent over-heating of the valve assembly. The emergency shut-off system may be configured to detect a potential for over-heating (e.g., based on a temperature measurement exceeding a threshold, a specified duration, etc.) and, in response to detecting that potential, alter some operation of the regulator, the heating element, the system itself, and/or the like. In embodiments, the emergency shut-off system may be a separate system, integrated with the regulator, and/or the like. For example, in embodiments, the emergency shut-off system may include functionality built into the regulator that is configured to facilitate safe operation thereof.

In embodiments, the regulator may be configured to perform the thermal disinfection cycle automatically at start-up. Embodiments of the method 300 also include performing a self-diagnosis process (304), which may be performed automatically at start-up (before, during, or after the thermal disinfection cycle). As is further shown in FIG. 3, the method 300 may include performing an operational task 306 and maintaining, during performance of at least a portion of the operational task, the temperature of the regulator valve assembly at a target temperature (block 308). In embodiments, performing the operational task may include, for example, applying a vacuum to a blood (e.g., venous) reservoir and controlling a valve assembly to control the applied vacuum. In embodiments, therefore, the method may further include directly measuring the pressure in the reservoir, where directly measuring the pressure includes utilizing a sensing tube directly connected to the reservoir.

According to embodiments, the regulator may utilize a heating/cooling element to facilitate control of the temperature of the valve assembly. For example, in embodiments, a valve assembly temperature of approximately 70 degrees Celsius can be constantly maintained, for example, to kill bacteria and/or prevent condensation throughout the operational task to facilitate maintenance of dry inner surfaces of the valve assembly. The control unit may be configured to utilize at least one of a look-up table and a control mechanism (e.g., a feedback control algorithm, etc.) to facilitate maintaining the temperature of the valve assembly at a target temperature. Embodiments of the method 300 may further include facilitating cooling the valve assembly to a cooling temperature, the cooling temperature being a temperature selected to prevent condensation on inner surfaces of the valve assembly in response to contact with aspirated air. In embodiments, heating, cooling, and/or maintaining the temperature of the valve assembly may include utilizing electrical heating and/or a Peltier element.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The invention claimed is:

1. A method, performed by a controller for controlling vacuum in a reservoir to facilitate vacuum assisted venous drainage, the method comprising:
   performing a thermal disinfection cycle by heating a valve assembly to a target temperature;
   performing an operational task; and
   maintaining, during performance of at least a portion of the operational task, a temperature of the valve assembly at the target temperature.

2. The method of claim 1, wherein maintaining the temperature comprises utilizing electrical heating or a Peltier element.

3. The method of claim 1, wherein maintaining the temperature comprises:
  heating the valve assembly to the target temperature; and
  maintaining the valve assembly at the target temperature for a specified duration.

4. The method of claim 1, further comprising:
  facilitating cooling the valve assembly to a cooling temperature, the cooling temperature being a temperature selected to prevent condensation on inner surfaces of the valve assembly in response to contact with aspirated air.

5. The method of claim 4, wherein facilitating cooling the valve assembly comprises controlling a Peltier element.

6. The method of claim 1, wherein maintaining the temperature comprises utilizing at least one of a look-up table and a feedback control mechanism.

7. The method of claim 6, wherein the feedback control mechanism comprises a proportional integral derivative algorithm.

8. The method of claim 1, further comprising directly measuring the pressure in the reservoir.

9. A method of controlling a vacuum assisted venous drainage system, the method comprising:
  initiating a thermal disinfection cycle of a valve assembly using a controller, which includes heating the valve assembly to a target temperature; and
  maintaining a temperature of the valve assembly at the target temperature for a specified duration while performing an operational task with the vacuum assisted venous drainage system, wherein the operational task includes applying a vacuum to a blood reservoir of the vacuum assisted venous drainage system.

10. The method of claim 9, wherein the controller initiates the thermal disinfection cycle during a start-up procedure of the vacuum assisted venous drainage system.

11. The method of claim 9, further comprising:
  providing the temperature of the valve assembly to the controller with a temperature sensor during the thermal disinfection cycle.

12. The method of claim 9, wherein after the specified duration, the controller initiates cooling the valve assembly to a cooling temperature, the cooling temperature being a temperature selected to prevent condensation on inner surfaces of the valve assembly.

13. The method of claim 9, wherein the target temperature is 90 degrees C. or more.

14. The method of claim 13, wherein the specified duration is 5 minutes or more.

15. A method of controlling a vacuum assisted venous drainage system, the method comprising:
  initiating a thermal disinfection cycle of a valve assembly of a vacuum regulator using a controller during a start-up procedure of the vacuum assisted venous drainage system, wherein initiating the thermal disinfection cycle includes heating the valve assembly to a target temperature for a specified duration; and
  applying a vacuum to the vacuum regulator while maintaining the target temperature.

16. The method of claim 15, further comprising:
  initiating cooling the valve assembly to a cooling temperature using the controller upon completion of the thermal disinfection cycle, the cooling temperature being a temperature selected to prevent condensation on inner surfaces of the valve assembly.

17. The method of claim 15, further comprising:
  providing a temperature of the valve assembly to the controller with a temperature sensor during the thermal disinfection cycle.

18. The method of claim 15, wherein the target temperature is 90 degrees C. or more.

19. The method of claim 18, wherein the specified duration is 5 minutes or more.

* * * * *